US006913619B2

(12) United States Patent
Brown et al.

(10) Patent No.: US 6,913,619 B2
(45) Date of Patent: Jul. 5, 2005

(54) LONGITUDINALLY FLEXIBLE EXPANDABLE STENT

(75) Inventors: Brian J. Brown, Hanover, MN (US); Michael L. Davis, Shorewood, MN (US)

(73) Assignee: Boston Scientific SciMed, Inc., Maple Grove, MN (US)

(*) Notice: Subject to any disclaimer, the term of this patent is extended or adjusted under 35 U.S.C. 154(b) by 0 days.

(21) Appl. No.: 10/194,854

(22) Filed: Jul. 11, 2002

(65) Prior Publication Data

US 2002/0177893 A1 Nov. 28, 2002

Related U.S. Application Data

(63) Continuation of application No. 08/511,076, filed on Aug. 3, 1995, now Pat. No. 6,818,014, which is a continuation-in-part of application No. 08/396,569, filed on Mar. 1, 1995, now abandoned.

(51) Int. Cl.$^7$ .................................................. A61F 2/06
(52) U.S. Cl. ..................................... 623/1.16; 623/1.15
(58) Field of Search ............................. 623/1.15, 1.16, 623/1.18, 1.19

(56) References Cited

U.S. PATENT DOCUMENTS

| | | |
|---|---|---|
| 2,836,181 A | 5/1958 | Tapp |
| 3,105,492 A | 10/1963 | Jeckel |
| 3,272,204 A | 9/1966 | Arnandi et al. |
| 3,490,975 A | 1/1970 | Lightwood et al. |
| 3,509,883 A | 5/1970 | Dibelius |
| 3,526,228 A | 9/1970 | Lyng |
| 3,562,820 A | 2/1971 | Braun |
| 3,635,215 A | 1/1972 | Shea et al. |
| 3,657,744 A | 4/1972 | Ersek |
| 3,771,526 A | 11/1973 | Rudle |
| 3,868,956 A | 3/1975 | Alfidi et al. |
| 3,993,078 A | 11/1976 | Bergentz et al. |
| 4,078,167 A | 3/1978 | Banas et al. |

(Continued)

FOREIGN PATENT DOCUMENTS

| | | |
|---|---|---|
| EP | 0 364 787 B1 | 4/1990 |
| EP | 0 540 290 A2 | 5/1993 |
| EP | 0 541 443 A1 | 5/1993 |
| EP | 0 606 165 A1 | 7/1994 |
| JP | 6-4175 | 3/1994 |
| WO | WO 94/17754 | 8/1994 |

OTHER PUBLICATIONS

U.S. Appl. No. 09/197,278, filed Nov. 20, 1998, Brown et al.
U.S. Appl. No. 09/599,674, filed Jun. 22, 2000, Brown et al.

(Continued)

Primary Examiner—Paul B. Prebilic
(74) Attorney, Agent, or Firm—Vidas, Arrett & Steinkraus

(57) ABSTRACT

A stent comprises a plurality of adjacent cylindrical elements defining a first end section, a second end section, and a center section therebetween. Each cylindrical element has constant thickness struts formed in a generally serpentine wave pattern transverse to the longitudinal axis which contains alternating valley portions and peak portions. A plurality of interconnecting members extend between the adjacent cylindrical elements and connect the adjacent cylindrical elements to one another. The cylindrical elements are formed of a stent material, the composition of which is uniform throughout the stent. The stent material of the struts in each of the first end section and the second end section have a greater mass than the stent material of the struts of the center section.

4 Claims, 3 Drawing Sheets

U.S. PATENT DOCUMENTS

| | | | |
|---|---|---|---|
| 4,127,761 A | 11/1978 | Pauley et al. | |
| 4,130,904 A | 12/1978 | Whalen | |
| 4,140,126 A | 2/1979 | Choudhury | |
| 4,141,364 A | 2/1979 | Schultze | |
| 4,164,045 A | 8/1979 | Bokros et al. | |
| 4,214,587 A | 7/1980 | Sakura, Jr. | |
| 4,300,244 A | 11/1981 | Bokros | |
| 4,313,231 A | 2/1982 | Koyamada | |
| 4,319,363 A | 3/1982 | Ketharanathan | |
| 4,425,908 A | 1/1984 | Simon | |
| 4,441,215 A | 4/1984 | Kaster | |
| 4,470,407 A | 9/1984 | Hussein | |
| 4,501,264 A | 2/1985 | Rockey | |
| 4,503,569 A | 3/1985 | Dotter | |
| 4,512,338 A | 4/1985 | Balko et al. | |
| 4,535,770 A | 8/1985 | Lemole | |
| 4,550,447 A | 11/1985 | Seiler, Jr. et al. | |
| 4,553,545 A | 11/1985 | Maass et al. | |
| 4,560,374 A | 12/1985 | Hammerslag | |
| 4,580,568 A | 4/1986 | Gianturco | |
| 4,597,389 A | 7/1986 | Ibrahim et al. | |
| 4,647,416 A | 3/1987 | Seiler, Jr. et al. | |
| 4,649,922 A | 3/1987 | Wiktor | |
| 4,655,771 A | 4/1987 | Wallsten | |
| 4,655,776 A | 4/1987 | Lesinski | |
| 4,665,906 A * | 5/1987 | Jervis | 606/78 |
| 4,665,918 A | 5/1987 | Garza et al. | |
| 4,681,110 A | 7/1987 | Wiktor | |
| 4,693,721 A | 9/1987 | Ducheyne | |
| 4,733,665 A | 3/1988 | Palmaz | |
| 4,739,762 A | 4/1988 | Palmaz | |
| 4,740,207 A | 4/1988 | Kreamer | |
| 4,760,849 A | 8/1988 | Kropf | |
| 4,762,128 A | 8/1988 | Rosenbluth | |
| 4,768,507 A * | 9/1988 | Fischell et al. | 623/1.11 |
| 4,769,029 A | 9/1988 | Patel | |
| 4,771,773 A | 9/1988 | Kropf | |
| 4,776,337 A | 10/1988 | Palmaz | |
| 4,786,507 A | 11/1988 | Schmidt | |
| 4,787,899 A | 11/1988 | Lazarus | |
| 4,795,458 A | 1/1989 | Regan | |
| 4,795,465 A | 1/1989 | Marten | |
| 4,800,882 A | 1/1989 | Gianturco | |
| 4,820,298 A | 4/1989 | Leveen et al. | |
| 4,830,003 A | 5/1989 | Wolff et al. | |
| 4,842,575 A | 6/1989 | Hoffman, Jr. et al. | |
| 4,848,343 A | 7/1989 | Wallsten et al. | |
| 4,851,009 A | 7/1989 | Pinchuk | |
| 4,856,516 A | 8/1989 | Hillstead | |
| 4,872,874 A | 10/1989 | Taheri | |
| 4,877,030 A | 10/1989 | Beck et al. | |
| 4,878,906 A | 11/1989 | Lindemann et al. | |
| 4,886,062 A | 12/1989 | Wiktor | |
| 4,913,141 A | 4/1990 | Hillstead | |
| 4,922,905 A | 5/1990 | Strecker | |
| 4,950,227 A | 8/1990 | Savin et al. | |
| 4,950,258 A | 8/1990 | Kawai et al. | |
| 4,994,071 A | 2/1991 | MacGregor | |
| 5,015,253 A | 5/1991 | MacGregor | |
| 5,019,090 A | 5/1991 | Pinchuk | |
| 5,035,706 A | 7/1991 | Gianturco et al. | |
| 5,037,392 A | 8/1991 | Hillstead | |
| 5,059,211 A | 10/1991 | Stack et al. | |
| 5,064,435 A | 11/1991 | Porter | |
| 5,071,407 A * | 12/1991 | Termin et al. | 604/104 |
| 5,089,005 A * | 2/1992 | Harada | 606/194 |
| 5,092,877 A | 3/1992 | Pinchuk | |
| 5,102,417 A | 4/1992 | Palmaz | |
| 5,104,399 A | 4/1992 | Lazarus | |
| 5,104,404 A | 4/1992 | Wolff | |
| 5,108,415 A | 4/1992 | Pinchuk et al. | |
| 5,108,417 A | 4/1992 | Sawyer | |
| 5,122,154 A | 6/1992 | Rhodes | |
| 5,133,732 A | 7/1992 | Wiktor | |
| 5,135,536 A | 8/1992 | Hillstead | |
| 5,139,480 A | 8/1992 | Hickle et al. | |
| 5,147,385 A | 9/1992 | Beck et al. | |
| 5,147,400 A | 9/1992 | Kaplan et al. | |
| 5,158,548 A | 10/1992 | Lau et al. | |
| 5,163,952 A | 11/1992 | Froix | |
| 5,195,984 A | 3/1993 | Schatz | |
| 5,197,978 A | 3/1993 | Hess | |
| 5,217,483 A | 6/1993 | Tower | |
| 5,226,913 A | 7/1993 | Pinchuk | |
| 5,282,823 A | 2/1994 | Schwartz et al. | |
| 5,282,824 A | 2/1994 | Gianturco | |
| 5,292,331 A | 3/1994 | Boneau | |
| 5,304,200 A | 4/1994 | Spaulding | |
| 5,344,425 A | 9/1994 | Sawyer | |
| 5,354,308 A | 10/1994 | Simon et al. | |
| 5,354,309 A | 10/1994 | Schnepp-Pesch et al. | |
| 5,356,423 A * | 10/1994 | Tihon et al. | 623/1.15 |
| 5,383,892 A | 1/1995 | Cardon et al. | |
| 5,389,106 A * | 2/1995 | Tower | 623/1.15 |
| 5,405,377 A | 4/1995 | Cragg | |
| 5,449,373 A | 9/1995 | Pinchasik et al. | |
| 5,527,354 A * | 6/1996 | Fontaine et al. | 623/12 |
| 5,545,210 A * | 8/1996 | Hess et al. | 623/12 |
| 5,549,663 A * | 8/1996 | Cottone, Jr. | 623/12 |
| 5,554,181 A * | 9/1996 | Das | 623/1.12 |
| 5,591,197 A * | 1/1997 | Orth et al. | 623/1.16 |
| 5,630,829 A * | 5/1997 | Lauterjung | 623/1.15 |
| 5,643,312 A * | 7/1997 | Fischell et al. | 623/1.15 |
| 5,653,727 A * | 8/1997 | Wiktor | 623/1.15 |
| 5,716,365 A * | 2/1998 | Goicoechea et al. | 623/1.16 |
| 5,716,393 A * | 2/1998 | Lindenberg et al. | 623/1.2 |
| 5,718,724 A * | 2/1998 | Goicoechea et al. | 606/194 |
| 5,725,572 A * | 3/1998 | Lam et al. | 623/1.16 |
| 5,735,893 A * | 4/1998 | Lau et al. | 623/1.16 |
| 5,776,180 A * | 7/1998 | Goicoechea et al. | 606/36 |
| 5,800,508 A * | 9/1998 | Goicoechea et al. | 623/1.15 |
| 5,800,521 A * | 9/1998 | Orth | 623/1.23 |
| 5,876,432 A * | 3/1999 | Lau et al. | 623/1.13 |
| 5,902,317 A * | 5/1999 | Kleshinski et al. | 623/1.18 |
| 5,916,263 A * | 6/1999 | Goicoechea et al. | 623/1.11 |
| 5,938,696 A * | 8/1999 | Goicoechea et al. | 606/194 |
| 5,972,018 A * | 10/1999 | Israel et al. | 606/198 |
| 6,013,854 A * | 1/2000 | Moriuchi | 606/194 |
| 6,051,020 A * | 4/2000 | Goicoechea et al. | 623/1.35 |
| 6,156,052 A * | 12/2000 | Richter et al. | 606/191 |
| 6,273,911 B1 * | 8/2001 | Cox et al. | 623/1.15 |
| 6,348,065 B1 | 2/2002 | Brown et al. | 623/1.16 |
| 6,451,052 B1 * | 9/2002 | Burmeister et al. | 623/1.16 |
| 6,464,722 B2 * | 10/2002 | Israel et al. | 623/1.17 |
| 6,468,302 B2 * | 10/2002 | Cox et al. | 623/1.15 |
| 6,582,461 B1 * | 6/2003 | Burmeister et al. | 623/1.18 |
| 6,596,022 B2 * | 7/2003 | Lau et al. | 623/1.16 |
| 2002/0056298 A1 | 12/2001 | Brown et al. | 623/1.16 |
| 2002/0007212 A1 | 1/2002 | Brown et al. | 623/1.16 |

OTHER PUBLICATIONS

U.S. Appl. No. 09/666,866, filed Sep. 20, 2000, Brown et al.

*Manufacturing Processes for Engineering Materials*, by Serope Kalpakjian, Illinois Institute of Technology, Addison–Wesley Publishing Company, pp. 340.

*A View of Vascular Stents*, by Richard A. Schatz, MD, From the Arizona Heart Institute Foundation, Phoenix, Arizona, Circulation, vol. 79, No. 2, Feb. 1989, pp. 445–457.

*The Self–Expanding Mesh Stent*, by Ulrich Sigwart, SECTION IV, Chapter 29, pp. 605–610.

Japanese Infringement Search on Articulated Expandable Stents, Dated Jul. 12, 1995.

*Engineering Fluid Mechanics*, Third Edition, John A. Roberson and Clayton T. Crowe, pp. 94 and pp 414–421.

*Cambridge Dictionary of Science and Technology*, Cambridge University Pressp. 128.

*Improved Dilation Catheter Balloons*, by Stanley B. Levy, Ph.D., *Journal of Clinical Engineering*, vol. 11, No. 4, Jul.–Aug. 1986, pp. 291–296.

*Self–expanding Stainless Steel Biliary Stents*[1], By Harold G. Coons, MD, *Radiology 1989*, vol. 170, No. 3, Part 2, pp. 979–983.

Technical Note Entitled *Modifications of Gianturco Expandable Wire Stents*, By Barry T. Uchida et al., *AJR*, vol. 150, May 1988, pp. 1185–1187.

Brochure from Cook Incorporated regarding Gianturco–Rosch Biliary Z–Stents™.

*Expandable Biliary Endoprosthesis: An Experimental Study*, By Carrasco et al., *AJR*, vol. 145, Dec. 1985, pp. 1279–1282.

*Gianturco Expandable Metallic Biliary Stents: Results of a European Clinical Trial*[1], By Irving, et al., *Interventional Radiology*, vol. 172, No. 2, Aug. 1989, pp. 321–326.

*Tracheobronchial Tree: Expandable Metallic Stents Used in Experimental and Clinical Applications*[1], *Work in Progress*, By Wallace et al., *Radiology*, Feb. 1986, pp. 309–312.

Brochure Entitled *AVE Micro Stent* ™, Instructions for Use, By Applied Fascular Engineering, Inc., pp. 1–15.

Brochure Entitled *Micro Stent*™, By Applied Vascular Engineering, Inc.

Starck, E., "First Clinical Experience with the Memotherm Vascular Stent", *STENTS State of the Art Future Developments*, pp. 59–62 (Jun. 1995).

Melzer, A. et al., Performance Improvement of Surgical Instrumentation Through the Use of Ni–Ti Materials, *Proceedings of SMST–94 The First International Conference on Shape Memory and Superelastic Technologies*, pp. 401–409 (Mar. 7–10, 1994).

* cited by examiner

LONGITUDINALLY FLEXIBLE EXPANDABLE STENT

This application is Continuation of application Ser. No. 08/511,076, filed Aug. 3, 1995, now U.S. Pat. No. 6,818,014, which is a Continuation-In-Part of application Ser. No. 08/396,569, filed Mar. 1, 1995, now abandoned, the disclosures of which are hereby incorporated by reference.

FIELD OF THE INVENTION

This invention relates to an endoprosthesis device for implantation within a body vessel, typically a blood vessel. More specifically, it relates to a tubular expandable stent of improved longitudinal flexibility.

BACKGROUND OF THE INVENTION

Stents are placed or implanted within a blood vessel for treating stenoses, strictures or aneurysms therein. They are implanted to reinforce collapsing, partially occluded, weakened, or dilated sections of a blood vessel. They have also been implanted in the urinary tract and in bile ducts.

Typically, a stent will have an unexpanded (closed) diameter for placement and an expanded (opened) diameter after placement in the vessel or the duct. Some stents are self-expanding and some are expanded mechanically with radial outward force from within the stent, as by inflation of a balloon.

An example of the latter type is shown in U.S. Pat. No. 4,733,665 to Palmaz, which issued Mar. 29, 1988, and discloses a number of stent configurations for implantation with the aid of a catheter. The catheter includes an arrangement wherein a balloon inside the stent is inflated to expand the stent by plastically deforming it, after positioning it within a blood vessel.

A type of self-expanding stent is described in U.S. Pat. No. 4,503,569 to Dotter which issued Mar. 12, 1985, and discloses a shape memory stent which expands to an implanted configuration with a change in temperature. Other types of self-expanding stents not made of shape memory material are also known.

This invention is directed to stents of all these types when configured so as to be longitudinally flexible as described in detail hereinbelow. Flexibility is a desirable feature in a stent so as to conform to bends in a vessel. Such stents are known in the prior art. Examples are shown in U.S. Pat. No. 4,856,516 to Hillstead; U.S. Pat. No. 5,104,404 to Wolff; U.S. Pat. No. 4,994,071 to MacGregor; U.S. Pat. No. 5,102,417 to Palmaz; U.S. Pat. No. 5,195,984 to Schatz; U.S. Pat. No. 5,135,536 to Hillstead; U.S. Pat. No. 5,354,309 to Shepp-Pesch et al.; EPO Patent Application 0 540 290 A2 to Lau; EPO Patent Application No. 0 364 787 B1 to Schatz, and PCT Application WO 94/17754 (also identified as German Patent Application 43 03 181).

Generally speaking, these kinds of stents are articulated and are usually formed of a plurality of aligned, expandable, relatively inflexible, circular segments which are interconnected by flexible elements to form a generally tubular body which is capable of a degree of articulation or bending. Unfortunately, a problem with such stents is that binding, overlapping or interference can occur between adjacent segments on the inside of a bend due to the segments moving toward each other and into contact or on the outside of a bend the segments can move away from each other, leaving large gaps. This can lead to improper vessel support, vessel trauma, flow disturbance, kinking, balloon burst during expansion, and difficult recross for devices to be installed through already implanted devices and to unsupported regions of vessel.

A diamond configuration with diagonal connections between each and every diamond of each segment is also known but such closed configurations lack flexibility.

It is an object of this invention to provide a longitudinally flexible stent of open configuration that avoids these problems and exhibits improved flexibility (radially and longitudinally) in the stent body segments thereof rather than in flexible joints between the segments.

SUMMARY OF THE INVENTION

To this end, the invention provides a tubular expandable stent, comprising: a plurality of cylindrical shaped open cylindrical segments aligned on a common longitudinal axis to define a generally tubular stent body, each segment being defined by a member formed in an undulating flexible pattern of interconnected substantially parallel struts with pairs thereof having alternating interconnecting end portions to define the periphery of the expandable stent segment, and in which the connected end portions of paired struts in each segment, before the stent is expanded, are positioned substantially opposite to connected end portions of paired struts in adjacent segments. The segments are interconnected by a plurality of interconnecting elements extending from some of the connected end portions on one segment to some of the connected end portions on adjacent segments in such a manner that there are three or more legs between points of connection from one side of each segment to its other side. Additionally, the connecting elements extend angularly from connecting end portion of one segment to connecting end portion of an adjacent segment, not to an opposite connecting end portion on an adjacent segment, whereby upon expansion of the stent the adjacent segments are displaced relative to each other about the periphery of the stent body to accommodate flexing of the stent within paired struts without interference between adjacent segments, rather than by means of articulating flexible connectors between segments. As a result, the connectors between the segments are not intended to flex or bend under normal use.

BEST MODE DESCRIPTION OF THE INVENTION

Figure 1:
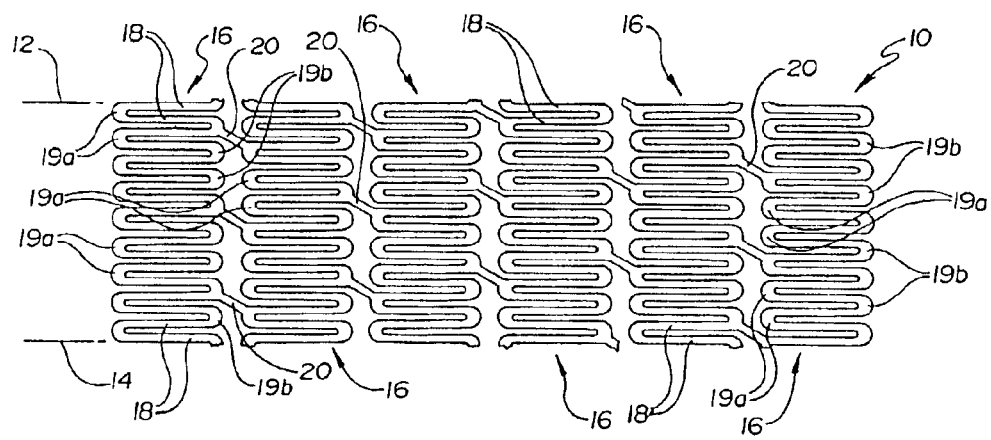
FIG. 1 shows a flat view of an unexpanded stent configuration according to the invention.
Figure 2:
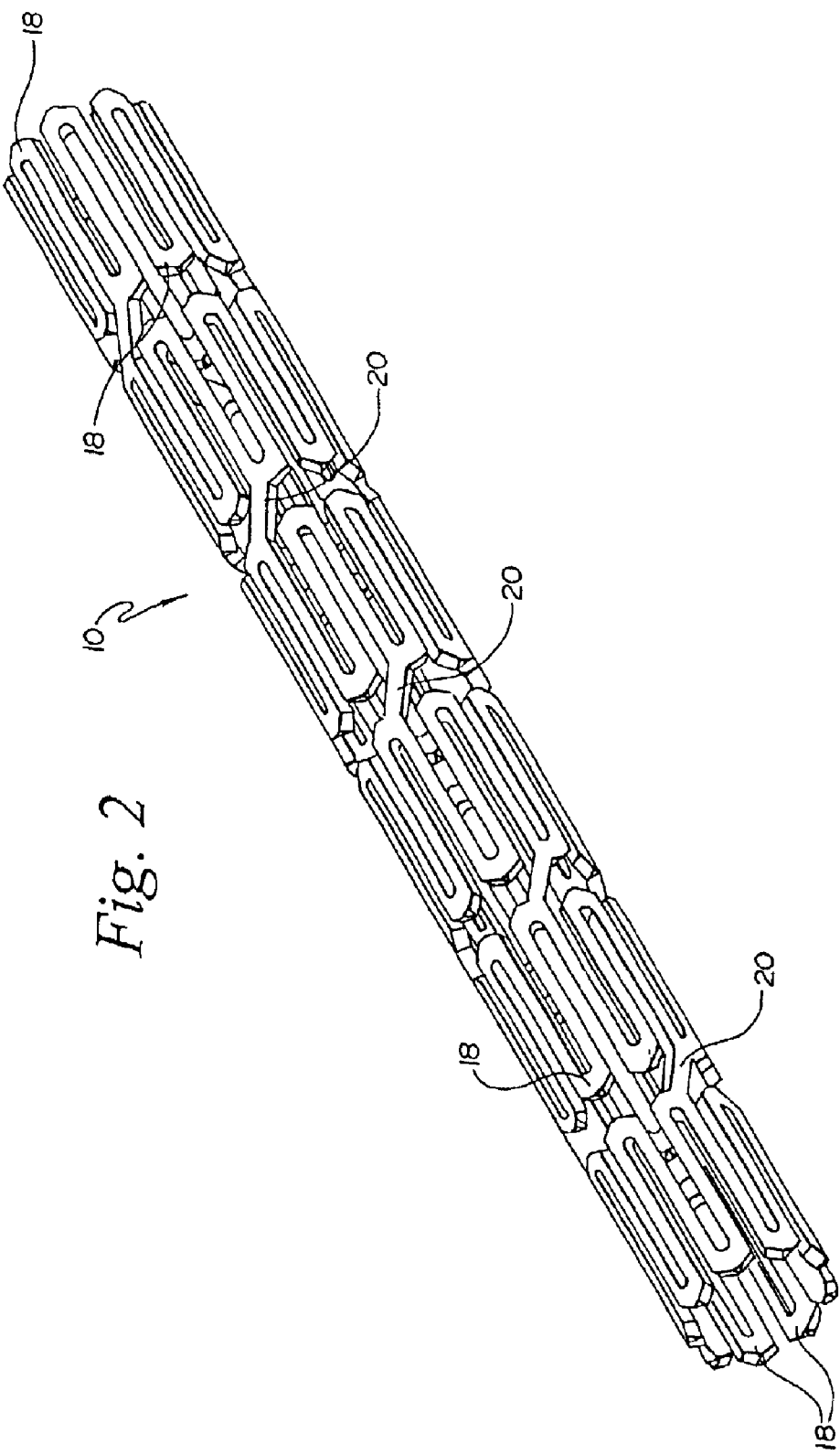
FIG. 2 shows the pattern of FIG. 1 in a tubular, unexpanded stent.

Turning to the Figures, FIG. 1 and FIG. 2 show a fragmentary flat view of an unexpanded stent configuration and the actual tubular stent (unexpanded), respectively. That is, the stent is shown for clarity in FIG. 1 in the flat and may be made from a flat pattern 10 (FIG. 1) which is formed into a tubular shape by rolling the pattern so as to bring edges 12 and 14 together (FIG. 1). The edges may then joined as by welding or the like to provide a configuration such as that shown in FIG. 2.

The configuration can be seen in these Figures to be made up of a plurality of adjacent segments generally indicated at 16, each of which is formed in an undulating flexible pattern of substantially parallel struts 18. Pairs of struts are interconnected at alternating end portions 19a and 19b. As is seen in FIG. 1, the interconnecting end portions 19b of one segment are positioned opposite interconnecting end portions 19a of adjacent segments. The end portions as shown are generally elliptical but may be rounded or square or pointed or the like. Any configuration of end portions is acceptable so long as it provides an undulating pattern, as shown. When the flat form 10 is formed into an unexpanded tube as shown in FIG. 2, the segments are cylindrical but the end portions 19 of adjacent segments remain in an opposed position relative to each other.

A more preferred method of manufacture begins with a thin walled tube which is then laser cut to provide the desired configuration. It may also be chemically etched or EDM'd (electrical discharge machined) to form an appropriate configuration.

Interconnecting elements 20 extend from one end portion 19 of one segment 16 to another end portion 19 of another adjacent segment 16 but not to an oppositely positioned end portion 19 of an adjacent segment 16. There are at least three struts included between the points on each side of a segment 16 at which an interconnecting element 20 contacts an end portion 19. This results in the interconnecting elements 20 extending in an angular direction between segments around the periphery of the tubular stent. Interconnecting elements 20 are preferably of the same length but may vary from one segment to the other. Also, the diagonal direction may reverse from one segment to another extending upwardly in one case and downwardly in another, although all connecting elements between any pair of segments are substantially parallel. FIG. 1, for example shows them extending downwardly, right to left. Upwardly would extend up left to right in this configuration.

Figure 3:
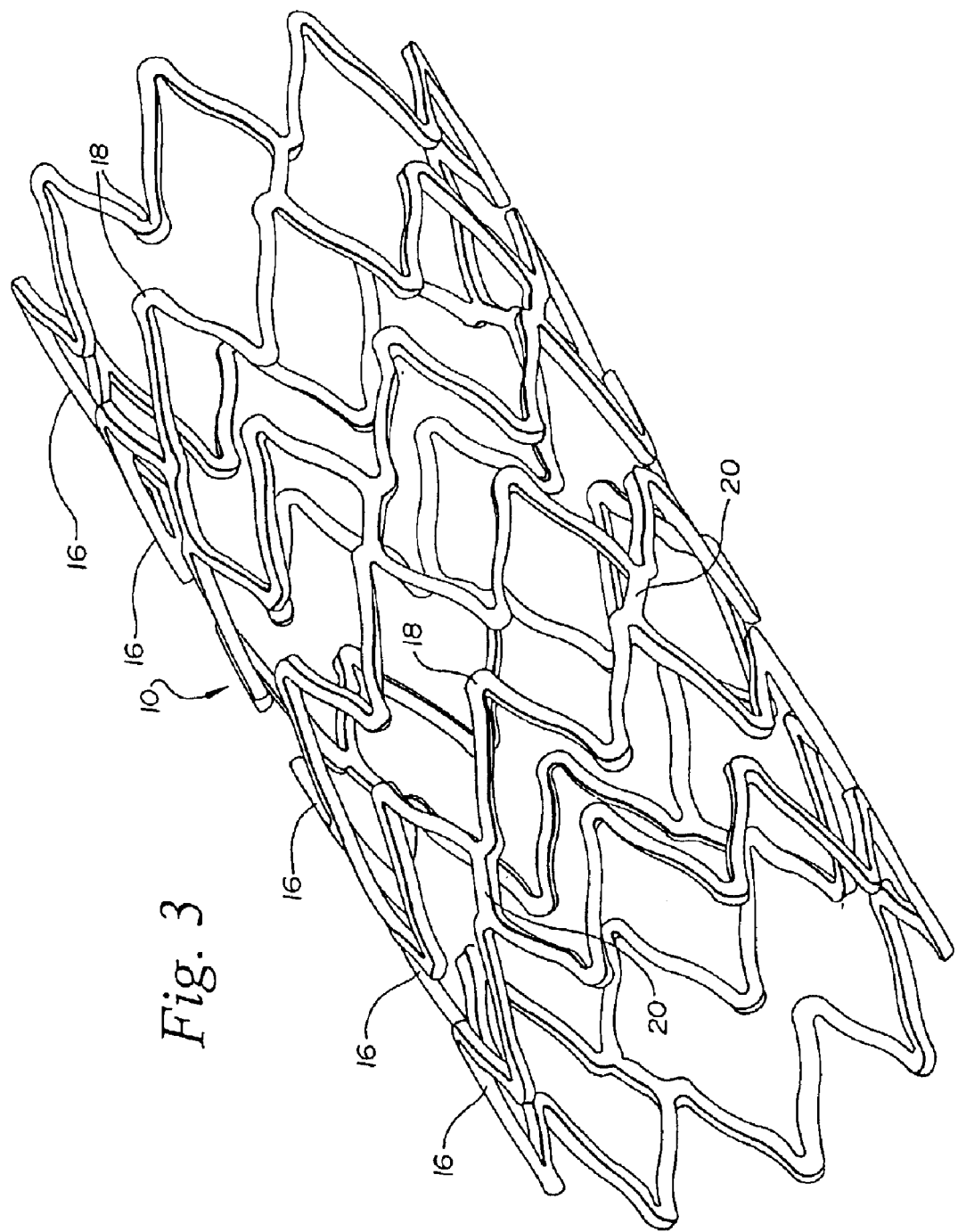
FIG. 3 shows an expanded stent of the configuration shown in FIG. 1.

As a result of this angular extension of the interconnecting elements 20 between adjacent segments and loops, upon expansion of the stent as seen in FIG. 3, the closest adjacent end portions 19 between segments 16 are displaced from each other and are no longer opposite each other so as to minimize the possibility of binding or overlapping between segments, i.e., pinching.

The number of interconnecting elements 20 may vary depending on circumstances in any particular instance. Three per segment are satisfactory for the configuration shown and at least three will be used typically.

Figure 4:
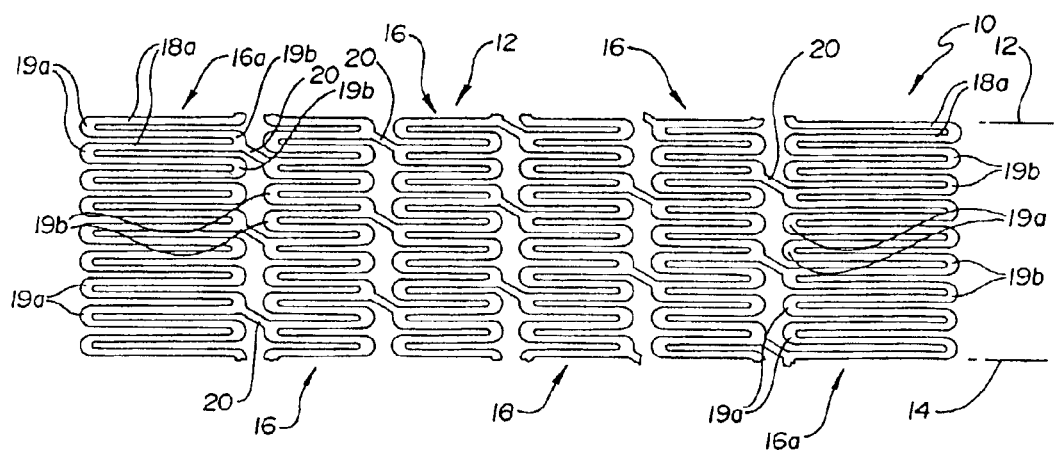
FIG. 4 shows a flat view of an alternate unexpanded stent configuration according to the invention.

The alternate design shown in FIG. 4 includes longer struts 18a in the two end segments 16a than in the intermediate segments 16. This allows the end segments (16a) to have less compression resistance than the intermediate segments (16), providing a more gradual transition from the native vessel to the support structure of the stent. The struts in the first end section have a greater mass than the struts of the center section and the struts in the second end section have a greater mass than the struts of the center section, as shown in FIG. 4. Otherwise, the configuration is the same as that shown in FIG. 1.

As already indicated, this invention is applicable to self-expanding configurations, mechanically expandable configurations and to a wide variety of materials, including both metal and plastic and any other material capable of functioning as an expandable stent. For example, the stent may be of metal wire or ribbon such as tantalum, stainless steel or the like. It may be thin-walled. It may be of shape memory alloy such as Nitinol or the like, etc.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent comprising:

a plurality of adjacent cylindrical elements defining a first end section, a second end section, and a center section therebetween;

each cylindrical element having constant thickness struts formed in a generally serpentine wave pattern transverse to the longitudinal axis and containing alternating valley portions and peak portions, each peak portion being curved along its entirety and connected to one valley portion by only a single straight strut and connected to another valley portion by another single straight strut, each vally portion being curved along its entirety and connected to one peak portion by only a single straight strut and connected to another peak portion by another single straight strut;

a plurality of interconnecting members extending between and connecting cylindrical elements which are adjacent one another; and wherein the cylindrical elements are formed of a stent material, the composition of which is uniform throughout the stent, the stent material of the struts in each of the first end section, and the second end section having a greater mass than the stent material of the struts of the center section, the struts of the cylindrical element in the first end section having a greater mass through a longer strut length than the struts of the cylindrical elements in the center section.

2. The stent of claim 1, wherein the stent is formed from a flat sheet from which material has been removed.

3. The stein of claim 1, wherein the stent is formed of a biocompatible material selected from the group consisting of stainless steel and nitinol.

4. The stent of claim 1, wherein the stent is formed from a single piece of tubing from which material has been removed.

* * * * *